(12) United States Patent
Hattori et al.

(10) Patent No.: US 7,173,144 B1
(45) Date of Patent: Feb. 6, 2007

(54) PROCESS FOR PRODUCING PHYTOSTEROLS BY SAPONIFICATION IN AN ALCOHOL/WATER SOLVENT

(75) Inventors: Yasuyuki Hattori, Wakayama (JP); Masamitsu Horio, Wakayama (JP); Jun Kono, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/129,279

(22) PCT Filed: Nov. 2, 2000

(86) PCT No.: PCT/JP00/07752

§ 371 (c)(1), (2), (4) Date: May 3, 2002

(87) PCT Pub. No.: WO01/32681

PCT Pub. Date: May 10, 2001

(30) Foreign Application Priority Data

Nov. 4, 1999 (JP) .................................. 11-313618

(51) Int. Cl.
*C07J 9/00* (2006.01)

(52) U.S. Cl. ..................................................... 552/545
(58) Field of Classification Search ................. 552/545
See application file for complete search history.

(56) References Cited

U.S. PATENT DOCUMENTS

| | | | |
|---|---|---|---|
| 2,715,639 A * | 8/1955 | Albrecht et al. | 260/397.25 |
| 2,835,682 A * | 5/1958 | Steiner et al. | 260/397.25 |
| 3,840,570 A | 10/1974 | Julian | |
| 5,763,353 A | 6/1998 | Kadono et al. | |
| 5,817,892 A | 10/1998 | Tamura et al. | |
| 6,383,970 B1 | 5/2002 | Mimura et al. | |
| 6,407,269 B2 | 6/2002 | Kaita et al. | |

FOREIGN PATENT DOCUMENTS

| | | |
|---|---|---|
| JP | 49 005959 | 1/1974 |
| JP | 52-8309 | 3/1977 |
| PL | 162 894 | 1/1994 |

OTHER PUBLICATIONS

Nekrasova et al., "Separation of phytosterol from aqueous alcohol solutions of saponified pitch by crystallization using the LTA method." Izv. Vys. Uch. Zav., Lesnoi Zhurnal, vol. 17(6), pp. 105-108 (English Abstract Only).*

Database Paperchem2 'Online! Institute of Paper Science and Technology (IPST); 1975 Nekrasova, V.B. et al.: "Separation of Phytosterol From Aqueous Alcohol Solutions of Saponified Pitch by Crystallization Using the LTA Method" retrieved from STN Database accession No. 2764 XP002161740 abstract & Izv. Vuz. Lesnoi Zh., (1974) vol. 17, No. 6, pp. 105-108, 'Russ.!., Abstract Only.

Database Biosis 'Online! Biosciences Information Service, Philadelphia, PA, US; 1993 Biedermann Maurus et al: "Transesterification and on-line LC-GC for determining the sum of free and esterified sterols in edible oils and fats." Database accession No. PREV199396027425 XP002161742 abstract & FETT Wissenschaft Technologie, vol. 95, No. 4, 1993, pp. 127-133, ISSN: 0931-5985, Abstract Only.

* cited by examiner

*Primary Examiner*—Barbara P. Badio
(74) *Attorney, Agent, or Firm*—Oblon, Spivak, McClelland, Maier & Neustadt, P.C.

(57) ABSTRACT

The present invention provides a method of obtaining highly pure phytosterols practically and efficiently from crude phytosterol compositions derived from vegetable fats and oils. That is, the present invention provides a method of saponifying fatty esters contained in crude phytosterol compositions with an alkali in a mixed solvent of an lower alcohol and water, as well as a process for producing phytosterols, which comprises, after this saponifying method, cooling the reaction solution to precipitate crystals of phytosterols, and separating the obtained crystals.

18 Claims, No Drawings

PROCESS FOR PRODUCING PHYTOSTEROLS BY SAPONIFICATION IN AN ALCOHOL/WATER SOLVENT

TECHNICAL FIELD

The present invention relates to a method of efficiently saponifying a fatty acid ester contained in a crude phytosterol composition derived from a vegetable fat and/or oil. Accordingly, it relates to a process for producing a highly pure phytosterol by using the saponified solution.

BACKGROUND ART

Phytosterols are not only used in clinical administration etc. expected to have an effect of reducing cholesterols in blood but also utilized as raw or starting materials for medicines as substitutes for cholesterols or as emulsifiers or emulsion-stabilizers in cosmetics and foods.

Sterols are contained in vegetable fats and oils such as a soybean oil, a rapeseed oil, a rice bran oil, a palm oil, a palm kernel oil and a coconut oil. There has been practically used a producing process by extraction and/or purification thereof from a deodorized concentrate etc. generated upon purification of fats and oils. JP-B 52-8309 describes a general method of extracting therefor. The method comprises adding a lower alcohol to a deodorized distillate of fats and oils in order to esterify with an acid catalyst, then washing with water to remove the acid catalyst, adding an additional lower alcohol and an alkali catalyst to carry out a transesterification reaction, further being calmly left overnight to precipitate crystals, separating the crystals by filtration, and washing and drying with hexane, in order to obtain phytosterols. And, it is described that the purity of the obtained phytosterols is 82%. However, the purity of the purified phytosterols is too low to be used directly as pharmaceutical preparations and food additives.

When methanol is particularly used as the lower alcohol for an esterification or transesterification reaction, methyl esters of $C_{6-28}$ fatty acids are contained as impurities in the resultant phytosterols. If these fatty acid methyl esters can be removed, a highly pure phytosterol can be obtained.

As a method of removing them, there is exemplified a saponification with an alkali. This method comprises converting a fatty ester with an alkali into a soap, precipitating a sterol crystal by cooling the soap, separating the crystal, and re-precipitating and drying the resultant crystal, in order to obtain a highly pure phytosterol. In this method, it is important how the saponification reaction is carried efficiently out, but, because of a low rate of saponification, the conventional method is not practical. Accordingly, the purification thereof by re-crystallizing repeatedly has been generally used in spite of an increasing number of steps. The problem of this method is that the yield of phytosterols is decreased thorough a number of steps, thus making the method uneconomical in respect of recovery.

DISCLOSURE OF INVENTION

The object of the present invention is to provide a method of obtaining a highly pure phytosterol practically and efficiently from a crude phytosterol composition derived from a vegetable fat and/or oil.

The present invention relates to a method of saponifying a fatty ester contained in a crude phytosterol composition with an alkali in a mixed solvent of a lower alcohol and water. It relates also to a process for producing a phytosterol, which comprises, after this saponifying method, cooling the reaction solution to precipitate crystals of the phytosterol and separating the obtained crystals.

In the present invention fatty acid esters, contained in a raw material of phytosterol, can be saponified and dissolved in the solvent mixture to remove the fatty acid esters and obtain a concentrated product of phytosterol. The invention relates to a process for producing phytosterol by cooling the above-shown saponification product mixture to obtain crystals of phytosterol and separating the crystals.

The present invention provides a process for producing a concentrated phytosterol product by treating a raw material with the above-mentioned saponifying process. The raw material may be fat and/or oil including fatty acid esters such as methyl ester. The product mixture of the saponification of the invention may be further purified by re-crystallization of natural phytosterol and the phytosterol product obtained by the saponification.

The invention is a purifying method of phytosterol and a concentrating method of a phytosterol in a fat and/or oil.

The present invention also provides a process for preparing a phytosterol product, comprising treating a crude phytosterol product including a fatty ester(s) with an alkali in a solvent mixture of a lower alcohol and water to saponify the fatty ester(s) contained in the crude phytosterol product. It is preferable that this process further comprises cooling the reaction solution to precipitate crystals of the phytosterol and separating the obtained crystals.

The starting crude phytosterol product used by the process of the invention may be in advance treated by (A) crystallizing the phytosterol in a solvent mixture of an organic solvent and water or (B) crystallizing the fatty acid esters in a lower alcohol at a temperature of 1 to 40° C., separating the crystals out and taking the lower alcohol solution including phytosterol. A more concentrated phytosterol product can be obtained this way.

MODES FOR CARRYING OUT THE INVENTION

The phytosterols in the present invention refer to sterols, contained in vegetable fats and oils, such as β-sitosterol, stigmasterol, campesterol and brassicasterol. A crude phytosterol composition refers to a phytosterol composition containing at least a fatty acid ester as impurity. The vegetable fat and/or oil as a raw material of the phytosterol is not limited in particular, but they are preferably a soybean oil, a rapeseed oil, a palm kernel oil, a coconut oil, a palm oil or the like.

The fatty acid esters in the present invention include mainly esters of higher fatty acids with lower alcohols and preferably include esters of $C_{6-28}$ fatty acids with $C_{1-4}$ lower alcohols. As the fatty acid in the present invention, there can be used any one selected from a member and a mixture of two or more members of leaner or branched saturated or unsaturated ones.

Examples of the lower alcohols in the present invention include methanol, ethanol, isopropanol, n-propanol and a linear or branched butanol. As the lower alcohol, there can be used a member or a mixture of two or more members thereof. Among them, methanol, ethanol or a mixture thereof is preferable and a methanol-containing member is particularly preferable.

Although the content of the fatty acid ester contained in the crude phytosterol composition is not particularly limited, the content is preferably not more than 50% by weight and more preferably not more than 30% by weight from the viewpoint of an efficiency of extracting sterols.

Further, the acid value (AV) based on a free fatty acid is detected in the crude phytosterol compositions. The acid value is preferably 10 or less, more preferably 5 or less, in order to highly concentrate the sterol. In addition, the content of phytosterols in the crude phytosterol compositions is preferably 50% by weight or more, more preferably 70% by weight or more.

In the present invention, fatty esters contained in the crude phytosterol compositions are saponified by treating with an alkali in a mixed solvent of a lower alcohol and water. The alkali used here is preferably potassium hydroxide, sodium hydroxide, sodium methylate or the like. To complete the reaction, it is necessary that the amount of the alkali used should be equal to or more than an equivalent calculated from the content of fatty esters contained in the crude phytosterol compositions. However, an excess amount of the alkali is not preferable from the viewpoint of an economy, and even by significantly increasing an amount of the alkali, a practical reaction rate cannot be obtained in the case that water is not added. Hence, the amount of the alkali is preferably 50 equivalents or less, more preferably 20 equivalents or less, as compared with the fatty esters contained in the crude phytosterol compositions.

In the present invention, the mixing ratio of water to the lower alcohol in a mixed solvent thereof used in the saponification is selected such that the amount of water is preferably 4% by weight or more, more preferably 8% by weight or more and most preferably 12% by weight or more as compared with that of the lower alcohol. If the ratio of water is increased, the degree of removal of fatty esters tends to be increased, but, from the viewpoint of crystallization and efficiency of facilities in the subsequent steps, it is preferably 100% by weight or less as compared with that of the lower alcohol.

Although the concentration of the crude phytosterol compositions as compared with that of the lower alcohol is not particularly limited, it is preferably 10% by weight or less from the viewpoint of solubility in the solvent.

Although the conditions for the saponification reaction in the present invention are not particularly limited, it is preferably carried out at 10 to 100° C. for 0.1 to 10 hours. It is preferable to use a batch-system reaction device in the reaction and it is advantageous from the viewpoint of the reaction temperature to reflux the solvent component during the reaction.

After the saponification reaction is finished, the reaction solution is cooled in the present invention to precipitate crystals of phytosterols. The crystals are separated then re-crystallized as necessary and dried if necessary, whereby highly pure phytosterols can be obtained.

It is preferable that the reaction solution is cooled with a cooling device and calmly left at 1 to 40° C. to precipitate the crystals. For example, the separation of the crystals is effected by a technique such as filtration, centrifugation and decantation. The crystals thus separated contain little alkali soap formed by the saponification reaction. Here, the alkali soap generated in the saponification reaction is hardly contained in the separated crystals, because most of the alkali soap is present as a dissolved form in the solvent. The re-crystallization can also be carried out using a publicly known solvent such as methanol. If necessary, the crystals are then dried. It is preferable to dry at a temperature of about 100° C. As the drying method is not particularly limited, the crystals are dried with hot air or the like.

The finally obtained product is a highly pure phytosterol being usable in both of a pharmaceutical preparation and a food additive.

By use of the saponifying method according to the present invention, the saponification reaction can be promoted by a mixed solvent of water and a lower alcohol, in order to complete the reaction at a practical rate. Further, by use of the process for producing phytosterols according to the present invention, fatty acid esters in phytosterols can be reduced to the detection limit or less so that highly pure phytosterols can be efficiently obtained practically from crude phytosterol compositions.

EXAMPLES

The term "%" in Examples is "% by weight" unless otherwise specified.

Example 1

As the raw material was used crude phytosterol compositions derived from a palm kernel oil possessing its acid value (AV) of 3.1, a saponification value (SV) of 18.9 and having the following composition: the purity of phytosterols was 84.3% (which refers to the total content of 4 kinds, that is, β-sitosterol, stigmasterol, campesterol and brassicasterol), the content of methyl ester-products of $C_{6-28}$ fatty acids was 10.5%, and the content of others was 5.2% (wherein the all contents were determined by a gas chromatography with a column ULTRA No. 1 (provided by Hewlett-Packard)).

2 g of the crude phytosterol compositions described above, the solvent comprising 200 g of methanol and 20 g of water, and 0.5 g of potassium hydroxide (wherein the amount of potassium hydroxide used here was 13-fold equivalents as compared with the fatty acid methyl esters because the amount of potassium hydroxide being equivalent to the fatty acid methyl esters was 0.039 g as determined by the saponification value) were introduced into a 1-L flask made of glass and reacted for 4 hours under a condition that the methanol was refluxed. The solution after the reaction was analyzed by a gas chromatography to determine the content of methyl esters of $C_{6-28}$ fatty acids. The result is shown in Table 1.

Example 2

The reaction and analysis were carried out in the same manner as in Example 1 except that the amount of water charged was 30 g. The result is shown in Table 1.

Example 3

The reaction and analysis were carried out in the same manner as in Example 1 except that the amount of water charged was 10 g. The result is shown in Table 1.

Example 4

The reaction and analysis were carried out in the same manner as in Example 1 except that the amount of the crude phytosterol compositions was doubled to be 4 g and consequently the amount of potassium hydroxide water was doubled to be 1.0 g. The result is shown in Table 1.

Example 5

The reaction and analysis were carried out in the same manner as in Example 1 except that the amount of water charged was 5 g. The result is shown in Table 1.

Comparative Example 1

The reaction and analysis were carried out in the same manner as in Example 1 except that water was not added. The result is shown in Table 1.

TABLE 1

| | Weight for charge | | | | Content of methyl esters of $C_{6-28}$ fatty acids after reaction for 4 hours |
|---|---|---|---|---|---|
| | Crude phytosterol composition | Potassium hydroxide | Methanol | Water (as compared with methanol *) | |
| Example 1 | 2 g | 0.5 g | 200 g | 20 g (10%) | 0.1% |
| Example 2 | 2 g | 0.5 g | 200 g | 30 g (15%) | Undetectable |
| Example 3 | 2 g | 0.5 g | 200 g | 10 g (5%) | 1.9% |
| Example 4 | 4 g | 1.0 g | 200 g | 20 g (10%) | Undetectable |
| Example 5 | 2 g | 0.5 g | 200 g | 5 g (2.5%) | 4.7% |
| Comparative Example 1 | 2 g | 0.5 g | 200 g | 0 g (0%) | 10.1% |

* [Weight of water] × 100/[weight of methanol]

It can be recognized from Table 1 that in Comparative Example where water is not added, the content of methyl esters is high after the reaction for 4 hours although the alkali is used in a large excess, while in Examples where water is added, the content of methyl esters is significantly reduced after the reaction for 4 hours.

Example 6

2 g of the same crude phytosterol compositions as in Example 1, the solvent comprising 200 g of ethanol and 20 g water, and 0.1 g of potassium hydroxide (the amount of potassium hydroxide used here was 2.6-fold equivalents as compared with the fatty acid methyl esters) were introduced into a 1-L flask made of glass and reacted for 4 hours under a condition that the methanol was refluxed. The solution after the reaction was analyzed by a gas chromatography to determine the content of methyl esters of $C_{6-28}$ fatty acids. The result is shown in Table 2.

Comparative Example 2

The reaction and analysis were carried out in the same manner as in Example 6 except that water was not added. The result is shown in Table 2.

TABLE 2

| | Weight for charge | | | | Content of methyl esters of $C_{6-28}$ fatty acids after reaction for 4 hours |
|---|---|---|---|---|---|
| | Crude phytosterol composition | Potassium hydroxide | Ethanol | Water (as compared with Ethanol *) | |
| Example 6 | 2 g | 0.1 g | 200 g | 20 g (10%) | 0.4% |
| Comparative Example 2 | 2 g | 0.1 g | 200 g | 0 g (0%) | 10.3% |

* [Weight of water] × 100/[weight of Ethanol]

Example 7

The product after the reaction for 4 hours in Example 4 was cooled to 5° C. to precipitate crystals, and the crystals were separated by a vacuum filter. The obtained crystals were dissolved in 200 g of methanol at 60° C., the solution was cooled to 5° C. to re-crystallize, and the resultant re-crystals were separated by a vacuum filter and dried in air at 110° C. for 12 hours. The purity of phytosterols in the crystals after drying was 95.8%, and no methyl esters of fatty acids could be detected by a gas chromatography. The recovery degree of the phytosterols in the process including the saponification step was 86.8%.

The invention claimed is:

1. A method of saponifying a fatty ester contained in a crude phytosterol composition with an alkali in a mixed solvent of a lower alcohol and water,
    wherein the acid value of the crude phytosterol compositions is 10 or less; and
    wherein a content of phytosterols in said crude phytosterol composition is 50% by weight or more.

2. The method as claimed in claim 1, wherein the content of water in the mixed solvent is 4% by weight or more per the lower alcohol.

3. The method as claimed in claim 1, wherein the fatty ester comprises esters of the $C_{6-28}$ fatty acids and lower alcohols.

4. The method of claim 1, further comprising cooling the reaction solution to precipitate crystals of the phytosterol and separating the obtained crystals.

5. A process for preparing a phytosterol product, comprising treating a crude phytosterol product including a fatty ester(s) with an alkali in a solvent mixture of a lower alcohol and water to saponify the fatty ester(s) contained in the crude phytosterol product, wherein the acid value of the crude phytosterol compositions is 10 or less; and wherein a content of phytosterols in said crude phytosterol composition is 50% by weight or more.

6. The process as claimed in claim 5, which further comprises cooling the reaction solution to precipitate crystals of the phytosterol and separating the obtained crystals.

7. The method of claim 1, wherein said phytosterol is at least one member selected from the group consisting of β-sitosterol, stigmasterol, campesterol and brassicasterol.

8. The method of claim 1, wherein said lower alcohol is at least one member selected from the group consisting methanol, ethanol, isopropanol, n-propanol, linear butanol and branched butanol.

9. The method of claim 1, wherein said lower alcohol is at least one member selected from the group consisting methanol and ethanol.

10. The method of claim 1, wherein said acid value is 5 or less.

11. The method of claim 1, wherein a content of phytosterols in said crude phytosterol composition is 70% by weight or more.

12. The method of claim 1, wherein said alkali is at least one member selected from the group consisting of potassium hydroxide, sodium hydroxide and sodium methylate.

13. The method of claim 1, wherein the amount of water is 100% by weight or less per the lower alcohol.

14. The method of claim 1, wherein the amount of water is 4% by weight or more and 100% by weight or less per the lower alcohol.

15. The method of claim 1, wherein the concentration of crude phytosterol compositions as compared with that of the lower alcohol is 10% by weight or less.

16. The method of claim 1, wherein saponifying is carried out at 10 to 100° C. for 0.1 to 10 hours.

17. A method of saponifying a fatty ester contained in a crude phytosterol composition with an alkali in a mixed solvent of a lower alcohol and water, wherein the acid value of the crude phytosterol compositions is 10 or less; and wherein the amount of alkali is 50 equivalents or less as compared with the fatty esters contained in said crude phytosterol composition; and wherein a content of phytosterols in said crude phytosterol composition is 50% by weight or more.

18. The method of claim 17, wherein the amount of alkali is 20 equivalents or less as compared with the fatty esters contained in said crude phytosterol composition.

* * * * *